United States Patent

Watson et al.

[11] 4,127,392
[45] Nov. 28, 1978

[54] METHANATION PROCESS START-UP

[75] Inventors: William B. Watson, Pittsburgh, Pa.; Richard G. Winter, Ponca City, Okla.; Geoffrey Twizell, Middlesex, England

[73] Assignee: Conoco Methanation Company, Stamford, Conn.

[21] Appl. No.: 847,998

[22] Filed: Nov. 2, 1977

[30] Foreign Application Priority Data

Feb. 27, 1977 [GB] United Kingdom ............... 7398/77

[51] Int. Cl.$^2$ ............................................. C10K 3/04
[52] U.S. Cl. ........................... 48/197 R; 260/449.6 M
[58] Field of Search ................. 48/197 R; 260/449 M, 260/449.6 M

[56] References Cited

U.S. PATENT DOCUMENTS

| 3,870,738 | 3/1975 | Tamanoto et al. | 260/449 M |
| 3,904,389 | 9/1975 | Banquy | 260/449 M |
| 3,967,936 | 7/1976 | Tajbl et al. | 260/449 M |
| 4,005,996 | 2/1977 | Hausberger et al. | 260/449 M |

FOREIGN PATENT DOCUMENTS 244,076  2/1927  United Kingdom ............... 260/449 M

OTHER PUBLICATIONS

"Methanation of Synthesis Gas", Seglin (Editor), 1974, 168th meeting of Division of Fuel Chem., ACS, pp. 87-90, 113-117, 123-130.

*Primary Examiner*—S. Leon Bashore
*Assistant Examiner*—Peter F. Kratz
*Attorney, Agent, or Firm*—F. Lindsey Scott; William A. Mikesell, Jr.

[57] ABSTRACT

A start-up method for a methanation process wherein a plurality of catalyst beds are used. The method comprises heating a first catalyst bed to a suitable temperature and thereafter charging a synthesis gas in mixture with an inert diluent to the first catalyst bed. The product stream from the first catalyst bed contains an excess of hydrogen and is passed to a second catalyst bed thereby heating the second catalyst bed. At least a portion of the product stream from the first catalyst bed is recycled to form the inert diluent used with the synthesis gas stream passed to the first catalyst bed.

8 Claims, 2 Drawing Figures

METHANATION PROCESS START-UP

This invention relates to a start-up method for multi-stage catalytic methanation processes.

In recent years it has become increasingly apparent that naturally occurring reserves of natural gas are finite and that the need for such fuels is increasing at a rapid pace. As a result of the increasing need for such fuels and the decreasing supply of natural gas, increasing attention has been directed to efforts to produce synthetic natural gas from coals and other carbonaceous materials. Some such processes are shown in U.S. Pat. No. 3,870,738 entitled "Process for Manufacturing Gases Rich in Methane" issued March 11, 1975 to Yamamoto et al. and U.S. Pat. No. 3,922,148 entitled "Production of Methane Gas" issued Nov. 25, 1975 to Child.

In the operation of such processes, it is difficult to start up the plant smoothly for a variety of reasons. The reactants charged to the catalyst typically comprise carbon dioxide, carbon monoxide, hydrogen, water and methane in varying proportions with the usual objective being the attainment of a stoichiometric balance between the hydrogen and carbon oxides charged so that the hydrogen and carbon oxides react to form methane. A variety of reactions occur in the catalyst bed which are of lesser interest, but the overall objective is the reaction of hydrogen with carbon oxides to form methane.

In the start-up of such processes it has been observed that in many instances, rapid temperature increases at the reactor inlet as a result of the entry of the synthesis gas can result in some instances in sintering of the catalyst, carbon deposits on the catalyst during the process start-up and the like. Such is clearly undesirable since such carbon deposits and sintering normally result in a marked decrease in catalyst activity. Further, the contact of carbon oxides and hydrogen with nickel and nickel compounds as commonly used in methanation catalysts under certain conditions, results in the formation of the extremely poisonous nickel carbonyl at low temperatures.

As a result of these difficulties, improved methods have continually been sought for starting up multi-stage methanation processes so that carbon deposits on the catalyst, sintering, high temperature catalyst deactivation, and the formation of nickel carbonyl are minimized.

It has now been found that these objectives are accomplished in a start-up method for a multi-stage methanation process utilizing a methanation catalyst comprising nickel, nickel compounds and the like supported on a suitable carrier by a method including the steps of:

(a) heating the first methanation catalyst bed to a temperature greater than about 400° F. (205° C.), (b) charging a mixture containing a synthesis gas in mixture with an inert diluent to the first catalyst bed with the synthesis gas being mixed with the inert diluent in an amount determined by the upper temperature limits in the catalyst bed, (c) recovering a reaction product from the first catalyst bed, (d) recycling at least a portion of the reaction product as the inert diluent mixed with the synthesis gas, (e) gradually adjusting the amount of synthesis gas and inert diluent charged to the first catalyst bed until a desired temperature in the first catalyst bed is attained, (f) maintaining the hydrogen content of the mixture charged to the first catalyst bed at an amount such that the reaction product recovered from the first catalyst bed contains unreacted hydrogen, (g) charging at least a portion of the reaction product to a second catalyst bed; and, (h) recovering a second reaction product stream from the second catalyst bed.

In the discussion of the Figures, the same numbers will be used to refer to the same or similar components throughout.

Figure 1:
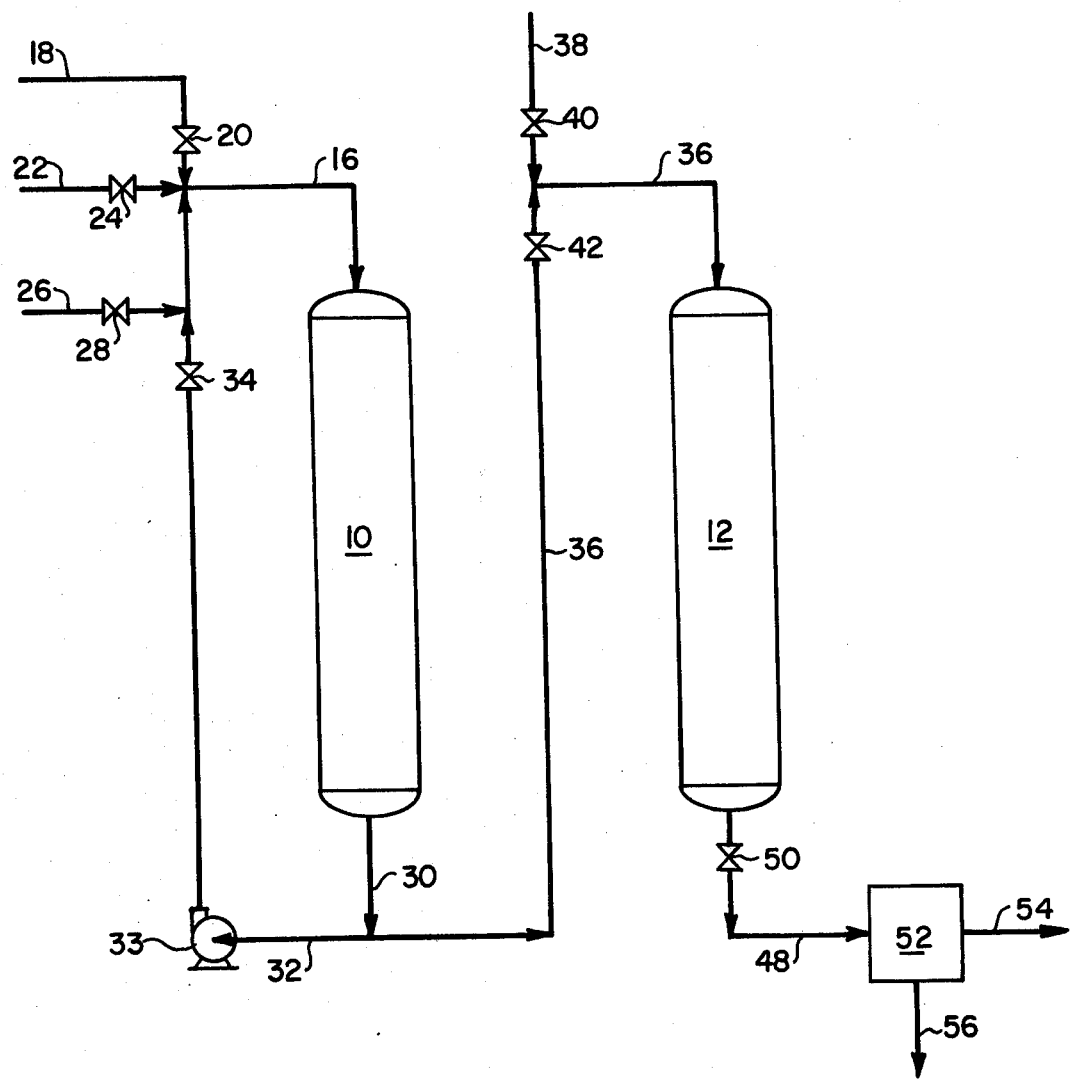
FIG. 1 is a schematic view of a methanation process using two reactors.
Figure 2:
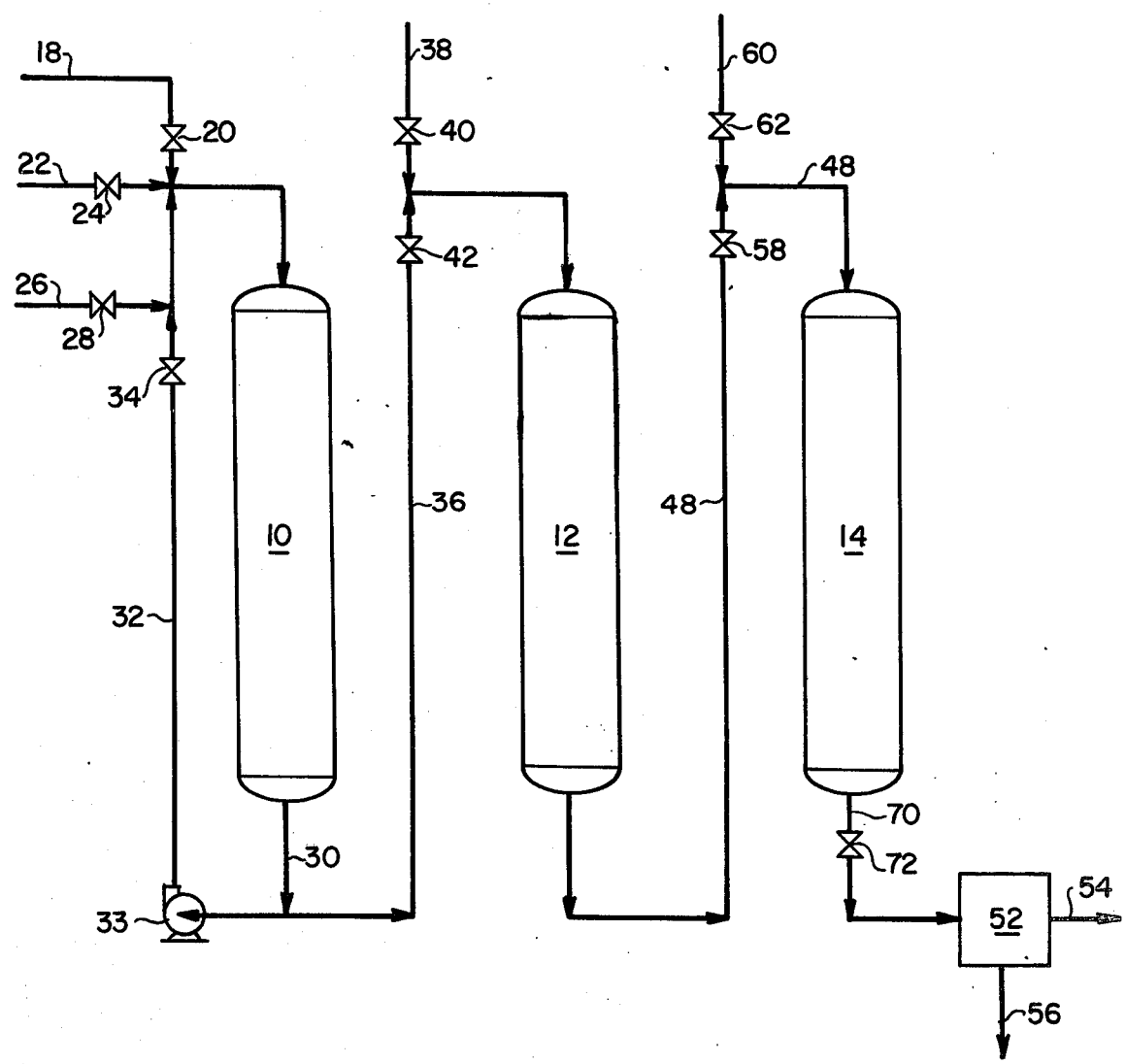
FIG. 2 is a schematic diagram of a methanation process utilizing three reactors.

In FIG. 1, a first reactor 10 and a second reactor 12 are shown as a part of a methanation process. FIG. 2 includes a third reactor 14.

Referring to FIG. 1, a first reactor 10 is connected to a first reactor inlet line 16 which is in fluid communication with a synthesis gas charge line 18 including a valve 20, a hydrogen charge line 22 including a valve 24, and an inert diluent charge line 26 including a valve 28. First reactor 10 is also provided with an outlet line 30, with outlet line 30 being in fluid communication with a product recycle line 32 which includes a compressor 33 and a valve 34. Outlet line 30 is also in fluid communication with a line 36 which includes valve 42 and is in fluid communication with a second reactor 12. A synthesis gas supply line 38 including a valve 40 is in fluid communication with line 36. Second reactor 12 includes a reactor outlet 48, including a valve 50, with reactor outlet 48 being in fluid communication with a water removal section 52 with methane being recovered from section 52 through a line 54 and water being recovered from section 53 through a line 56.

With respect to FIG. 2, first reactor 10 and second reactor 12 and the associated flow lines are substantially the same as in FIG. 1 except for the presence of a third reactor 14. In FIG. 2, line 48 carrying the product stream from second reactor 12 includes a valve 58 and is in fluid communication with third reactor 14. A synthesis gas line 60 including a valve 62 in fluid communication with line 48 is provided. A product stream is recovered from reactor 14 through a line 70, which includes a valve 72, and is passed to a water removal section 52 with methane being recovered through line 54 and water through line 56.

In the practice of the present invention, reactor 10 is heated to a temperature in excess of about 400° F. (205° C.) by any suitable technique. It has been found that one desirable technique is the use of a recirculating inert diluent stream, such as nitrogen or methane, heated by the use of an external heater. After heating the first catalyst bed to a temperature greater than 400° F. (205° C.), a mixture comprising a synthesis gas in mixture with an inert diluent is passed into a first catalyst bed positioned in reactor 10. The mixture comprises synthesis gas in mixture with an inert diluent such as nitrogen, methane, mixtures thereof and the like. The inert diluent is desirably selected from those materials commonly available which are non-reactive with the catalyst positioned in reactor 10. The synthesis gas stream typically comprises from about 10 to about 20 volume percent carbon monoxide, from about 0.5 to about 10 volume percent carbon dioxide, from about 35 to about 80 volume percent hydrogen, up to about 25 volume percent methane, and up to about 25 volume percent water. The synthesis gas is mixed with the inert diluent in an amount determined primarily by the permissible temperature rise in reactor 10. Desirably the temperature in the catalyst beds is not allowed to exceed about 750° F. during start-up. The amount of reactive material included in the mixture enables the calculation of the exothermic heat which will be generated upon reaction and allows the injection of a suitable amount of synthesis gas so that the upper temperature limits desired in the catalyst bed are achieved.

The exothermic reaction of the synthesis gas components in reactor 10 results in a further increase in the temperature in the reactor up to a desired maximum. The product stream from reactor 10 may be used as an inert diluent for mixture with the synthesis gas stream passed to reactor 10.

The hydrogen content of the mixture charged to reactor 10 should be sufficient to result in at least 10 volume percent and preferably at least about 20 volume percent unreacted hydrogen in the product stream recovered from reactor 10. Such is necessary to minimize the formation of nickel carbonyl, carbon deposits and the like in reactor 12 since at least a portion of the product stream from reactor 10 is used to heat reactor 12. If the synthesis gas contains an insufficient amount of hydrogen to attain the requisite unreacted hydrogen content in the product stream recovered from reactor 10, additional hydrogen may be introduced into the mixture charged to reactor 10 via hydrogen charge line 22. The presence of the unreacted hydrogen in the product stream results in a product stream from reactor 10 which contains essentially no carbon monoxide and very little carbon dioxide, i.e. less than about 2.0 volume percent, and preferably less than 0.5 volume percent carbon dioxide. Such is necessary since the presence of carbon oxides in the stream recovered from reactor 10 and passed to reactor 12 to heat reactor 12 could possibly result in the formation of poisonous nickel carbonyl if the excess hydrogen was not present to ensure essentially complete reaction of the carbon oxides charged to reactor 10 to other products which are non-reactive with the nickel catalyst to form nickel carbonyl. Clearly, one desirable method for heating reactor 12 is to pass the products from reactor 10 therethrough.

The product stream recovered from reactor 12 is passed to a water recovery zone in order that water may be removed from the methane produced. The product from the startup may contain undesirable quantities of nitrogen and the like and, if so, will require blending with additional methane for use as a high Btu fuel or it can be used as a low Btu fuel or the like.

As soon as the operating temperature of reactor 10 and reactor 12 have reached a temperature in excess of a desired minimum, then the hydrogen content of the mixture charged to reactor 10 can be reduced to an amount such that the product stream recovered from reactor 12 has a hydrogen content below 5 volume percent. Such is desirable in order that the use of excessive amounts of hydrogen can be eliminated and in order that the recovered methane will be of a high Btu value.

In a desirable option after start-up, synthesis gas is introduced into reactor 12 through line 38 as well as into reactor 10 in order that both reactors may be used to convert carbon oxides and hydrogen into methane. Of course, in those instances where extremely high conversion rates are desired, both reactors may be used in series (with no additional synthesis gas addition to reactor 12) to ensure that the reaction is substantially complete. Such variations and modifications are within the skill of those in the art, dependent upon the particular objective to be achieved.

In FIG. 2, the operation of reactors 10 and 12 is substantially as set forth above with the start-up of reactor 14 proceeding in the same manner as reactor 12 in that the products recovered from reactor 10 are passed through reactor 12 to heat reactor 12 and then on through reactor 14 to heat reactor 14. It is necessary that the hydrogen injected with the mixture injected into reactor 10 be sufficient to result in at least 10 volume percent and preferably at least about 20 volume percent unreacted hydrogen in the product stream recovered from reactor 14 until reactors 12 and 14 have reached a temperature in excess of about 400° F. (205° C.). Such is necessary as indicated previously to prevent the formation of nickel carbonyl by reaction of the synthesis gas over the cold nickel catalyst and the like.

By the use of the present invention, it is possible to introduce the synthesis gas into reactor 10 at a gradually increasing rate as the temperature of the catalyst bed increases so that the tendency to form carbon at the reactor inlet and the like during the reactor start-up is minimized. Further, the use of the method of the present invention allows the use of gradually increasing amounts of synthesis gas to increase the temperature gradually and utilize a portion of the product stream produced from the first reactor to replace the inert diluent used as a heat exchange medium at an early stage in the start-up proceedings.

Catalysts known to those skilled in the art are suitable in the method of the present invention. Some such catalysts are described in U.S. Pat. No. 3,890,113, issued June 17, 1975 to Child et al. which is hereby incorporated by reference.

Clearly, a larger number of reactors could be started up by the method of the present invention in a similar fashion and, of course, synthesis gas can be added to the inlet of each reactor after start-up if desired. While it is recognized that many of the unit steps of the present method have been used heretofore for the same or different objectives, it is pointed out that the particular combination of steps set forth herein has been found to be particularly effective in achieving reactor start-ups in multi-stage methanation processes with a minimal risk of carbon deposition on the catalyst during start-up, complete elimination of the possibility of high temperature deactivation of the catalyst, substantially no formation of nickel carbonyl and with a minimum use of undesirable inert diluents and resulting waste of reactant materials.

It is pointed out that while the present invention has been described with reference to specific preferred embodiments thereof, many variations and modifications are possible within the scope of the present invention and it is anticipated that many such variations and modifications may be considered obvious or desirable to those skilled in the art upon a review of the foregoing description of preferred embodiments.

Having thus described the invention, we claim:

1. A start-up method for a multi-stage methanation process wherein a methanation catalyst comprising nickel supported on a suitable catalyst carrier is used in a plurality of methanation catalyst beds, said method consisting essentially of sequentially:

(a) heating a first methanation catalyst bed to a temperature greater than 400° F.;

(b) charging a first mixture containing a synthesis gas stream comprising carbon oxides and hydrogen in mixture with an inert diluent stream to said first heated catalyst bed, said synthesis gas being mixed with said inert diluent stream in an amount fixed by the upper temperature limits in the catalyst bed;
(c) recovering a first reaction product stream from said first catalyst bed;
(d) recycling at least a portion of said first reaction product stream back to (b) as at least a portion of said inert diluent stream;
(e) gradually adjusting the amount of synthesis gas and inert diluent charged to said first catalyst bed until the temperature of said catalyst bed reaches a desired maximum temperature;
(f) maintaining the hydrogen content of said mixture at an amount such that said first reaction product stream contains at least about 10 volume percent unreacted hydrogen;
(g) charging at least a portion of said first reaction product stream containing at least about 10 volume percent unreacted hydrogen to a second catalyst bed to heat said second catalyst bed;
(h) recovering a second reaction product stream from said second catalyst bed; and,
(i) reducing the hydrogen content of said second reaction product stream to less than five volume percent after both said first catalyst bed and said second catalyst bed are above a desired minimum temperature. whereby said methanation process start-up is effected without the formation of nickel carbonyl and without carbon deposition on the catalyst.

2. The method of claim 1 wherein said first catalyst bed is heated by passing a heated inert diluent stream therethrough, said inert diluent being selected from the group consisting of nitrogen, methane and mixtures thereof.

3. The method of claim 2 wherein said inert diluent is nitrogen.

4. The method of claim 1 wherein said synthesis gas is present in said first mixture in an amount less than that required to raise the temperature in said first catalyst bed to 750° F.

5. The method of claim 1 wherein a plurality of reactors are started up by repeating steps (g) and (h).

6. The method of claim 1 wherein said synthesis gas contains from about 10 to about 20 volume percent CO, from about 0.5 to about 10 volume percent $CO_2$, from about 35 to about 80 volume percent $H_2$, and up to about 25 volume percent $H_2O$.

7. The method of claim 1 wherein synthesis gas is charged to said second catalyst bed after a desired minimum temperature in said second catalyst bed has been achieved.

8. The method of claim 7 wherein said minimum temperature in said second catalyst bed is greater than 400° F.

* * * * *